United States Patent
Bae et al.

(10) Patent No.: US 7,987,055 B2
(45) Date of Patent: Jul. 26, 2011

(54) BODY FAT MEASUREMENT DEVICE AND BODY FAT MEASUREMENT RESULT PROVIDING METHOD

(75) Inventors: Sang Kon Bae, Seoul (KR); In Duk Hwang, Suwon-si (KR); Sang Ryong Kim, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 193 days.

(21) Appl. No.: 11/976,620

(22) Filed: Oct. 25, 2007

(65) Prior Publication Data

US 2008/0103698 A1    May 1, 2008

(30) Foreign Application Priority Data

Oct. 30, 2006   (KR) .................. 10-2006-0105663

(51) Int. Cl.
     *G01N 33/48*      (2006.01)
(52) U.S. Cl. ............... 702/19; 702/21; 702/127
(58) Field of Classification Search ............ 702/19, 702/182, 188–189; 600/301, 347, 483, 485, 600/490; 128/920–921
See application file for complete search history.

(56) References Cited

U.S. PATENT DOCUMENTS

| | | | | |
|---|---|---|---|---|
| 4,850,365 A * | 7/1989 | Rosenthal | .................. | 600/473 |
| 2004/0260196 A1 * | 12/2004 | Lu | ................. | 600/547 |
| 2005/0014113 A1 * | 1/2005 | Fleck et al. | ............... | 434/247 |
| 2005/0080353 A1 * | 4/2005 | Whang et al. | ................ | 600/547 |
| 2005/0283051 A1 * | 12/2005 | Chen | ........................ | 600/300 |
| 2007/0239070 A1 * | 10/2007 | Hwang | ........................ | 600/587 |
| 2008/0183398 A1 * | 7/2008 | Petrucelli | ........................ | 702/19 |

FOREIGN PATENT DOCUMENTS

| | | |
|---|---|---|
| JP | 10-314144 | 12/1998 |
| JP | 11-004820 | 1/1999 |
| JP | 11-192214 | 7/1999 |
| JP | 2001-157670 | 6/2001 |
| JP | 2005-110962 | 4/2005 |
| JP | 2005-125059 | 5/2005 |
| KR | 10-2001-0069977 | 7/2001 |
| KR | 10-2004-0026780 | 4/2004 |
| KR | 10-2006-0032048 | 4/2006 |
| KR | 10-2006-0043704 | 5/2006 |
| KR | 10-2006-117443 | 11/2006 |

OTHER PUBLICATIONS

Korean Office Action for corresponding Korean Patent Application No. 10-2006-0105663 dated May 30, 2008 (4 pgs).

* cited by examiner

*Primary Examiner* — Drew A Dunn
*Assistant Examiner* — Mi'schita' Henson
(74) *Attorney, Agent, or Firm* — Staas & Halsey LLP

(57) ABSTRACT

A body fat measurement result providing method includes maintaining a body fat information database having stored therein at least one particular person's body fat information, which includes local body fat information for at least one body part of the at least one particular person, providing a user with a particular person list including the at least one particular person, and receiving a selection from the user of a first particular person selected from the particular person list, and generating a measurement result information by comparing the user's local body fat measured for at least one body part of the user, with corresponding local body fat information for the at least one body part of the first particular person.

28 Claims, 9 Drawing Sheets

FIG. 2

<BEYONCE'S BODY FAT INFORMATION>

| BODY PART | LOCAL BODY FAT INFORMATION |
|---|---|
| NECK | 6.3mm |
| TRICEPS | 9.8mm |
| BICEPS | 5.8mm |
| UPPER BACK | 8.9mm |
| FRONT CHEST | 8.1mm |
| LATERAL CHEST | 10.5mm |
| UPPER ABDOMEN | 12.8mm |
| LOWER ABDOMEN | 11.0mm |
| LOWER BACK | 7.9mm |
| HIP | 12.6mm |
| FRONT THIGH | 4.6mm |
| LATERAL THIGH | 5.1mm |
| REAR THIGH | 3.9mm |
| INNER THIGH | 6.3mm |
| CALF | 2.5mm |

FIG. 5

<FIRST MEASUREMENT RESULT INFORMATION-BEYONCE>

| BODY PART | LOCAL BODY FAT INFORMATION | GRAPH |
|---|---|---|
| NECK | 6.3mm | |
| TRICEPS | 9.8mm | |
| BICEPS | 5.8mm | |
| UPPER BACK | 8.9mm | |
| FRONT CHEST | 8.1mm | |
| LATERAL CHEST | 10.5mm | |
| UPPER ABDOMEN | 12.8mm | |
| LOWER ABDOMEN | 11.0mm | |
| LOWER BACK | 7.9mm | |
| HIP | 12.6mm | |
| FRONT THIGH | 4.6mm | |
| LATERAL THIGH | 5.1mm | |
| REAR THIGH | 3.9mm | |
| INNER THIGH | 6.3mm | |
| CALF | 2.5mm | |

KEY:
- ▨ : USER'S BODY FAT DATA
- ▧ : BEYONCE'S BODY FAT DATA

BODY FAT MEASUREMENT DEVICE AND BODY FAT MEASUREMENT RESULT PROVIDING METHOD

CROSS-REFERENCE TO RELATED APPLICATIONS

This application claims the benefit of Korean Patent Application No. 10-2006-0105663, filed on Oct. 30, 2006, in the Korean Intellectual Property Office, the disclosure of which is incorporated herein by reference.

BACKGROUND

1. Field

One or more embodiments of the present invention relate to a body fat measurement device and a body fat measurement result providing method. More particularly, one or more embodiments of the present invention relate to a body fat measurement device and a body fat measurement result providing method that can effectively manage a user's body fat and body shape by encouraging the user to control his diet. A user's local body fat is compared, for each of at least one body part, with a particular person's local body fat, the particular person being selected by the user as someone whom the user wants to appear similar to, and the comparison result is provided to the user.

2. Description of the Related Art

Currently, a greater proportion of people are obese or overweight, due to advancements in standard of living and lack of exercise. Being obese or overweight may lead to many adult diseases, and may also result in many types of discrimination. Accordingly, an increasing number of people are interested in dieting and in the treatment and prevention of obesity or being overweight, thereby rapidly expanding the scale of obesity-related industries. One of the main ways to measure a degree of obesity or being overweight is to measure the amount of a fat in a human body. Any person may recognize his or her relative degree of obesity by measuring body fat thickness, and may accordingly treat a measured level of obesity by going on a diet.

With the current fitness trend, a portable body fat measurement device has been developed and is currently used by a number of people. Such people may be able to measure their body fat at any time and place using a portable body fat measurement device, without seeing a doctor or going to a weight-loss clinic. Also, the portable body fat measurement device is mainly installed in mobile devices such as mobile phones; so people may conveniently and portably use the portable body fat measurement device.

One of the important purposes for measuring body fat is to encourage users to control their diet, exercise, and keep themselves in good shape by being aware of their body fat. However, in a conventional body fat measurement device, it is not easy for a user to determine whether a quantity of their body fat is normal since body fat measurement results are provided to users as only a numerical value.

Also, in the conventional body fat measurement device, the user is provided with the body fat measurement result by comparing a body fat of the user with a reference body fat value. Namely, the body fat measurement result is provided to the user by comparing the body fat of the user, for each body part, with reference values, which are predetermined depending on age, race, and gender. The reference values are generally acquired by making body fat measurements of a large number of people, and classifying the people according to their age, race, and gender. To collect such reference values, it is necessary to measure the body fat of the large number of people, acquire data from the measured body fat, and establish a range for each reference value in order to ensure a credible reference database, since body fat ratio, body fat thickness, and body shape differ depending on age, race, and gender. Thus, in the conventional body fat measurement device, it takes a great amount of time and cost to build a credible database. In addition, it is not simple to determine whether a person is normal or obese based on body fat data collected from a variety of people.

Also, in modern society, people have their own points of view and strive for individuality, rather than standardized points of view. Thus, not everyone wants a standardized body shape following a standardized database, even when the standardized database is built to vary with age, race, and gender. Particularly, teenage girls have their own opinions regarding body shape, and each teenage girl has a different reference value with respect to each of their body parts. As an example, a single teenage girl might want Angelina Jolie's bust for her bust shape, Beyonce's thighs for her thigh shape, and Cameron Diaz's legs for her leg shape. Accordingly, a standardized database is meaningless for teenage girls.

With the foregoing trends, a body fat measurement device that can effectively manage a user's body shape by motivating the user to control his or her diet and to steadily exercise, has been determined as desirable by the inventors of the present invention.

SUMMARY

One or more embodiments of the present invention provide a body fat measurement device and a body fat measurement result providing method that can encourage a user to effectively control his or her diet and to steadily exercise to achieve an ideal body shape, since local body fat, i.e., body fat in a particular body area, of a user is compared for each body part with local body fat of a particular person selected by the user, and the comparison result is provided to the user.

One or more embodiments of the present invention also provide a body fat measurement device and a body fat measurement result providing method that can encourage a user to effectively control his or her diet and to steadily exercise to achieve an ideal body shape, since local body fat, i.e., body fat in a particular body area, of a user is compared for each body part with local body fat of a particular person, selected by the user, the comparison result is provided to the user, and a user's desire to resemble a particular person for a respective body part is satisfied.

Additional aspects and/or advantages will be set forth in part in the description which follows and, in part, will be apparent from the description, or may be learned by practice of the invention.

To achieve at least the above and/or other aspects and advantages, embodiments of the present invention include a body fat measurement result providing method, the method including, maintaining a body fat information database having stored therein at least one particular person's body fat information, which includes local body fat information for at least one body part of the at least one particular person, providing a user with a particular person list including the at least one particular person, and receiving a selection from the user of a first particular person selected from the particular person list, and generating a measurement result information by comparing the user's local body fat measured for at least one body part of the user, with corresponding local body fat information for the at least one body part of the first particular person.

To achieve at least the above and/or other aspects and advantages, embodiments of the present invention include a body fat measurement result providing method, the method including, maintaining a body fat information database having stored therein at least one particular person's body fat information which includes local body fat information for at least one body part of the at least one particular person, providing the user with a particular person list, including the at least one particular person, via a predetermined user interface, and receiving a selection from the user for at least one body part and at least one particular person from the particular person list, generating a measurement result information by comparing local body fat information of a first body part, selected by the user, of a particular person, selected by the user, with corresponding local body fat information measured from the first body part of the user and by comparing local body fat information of a second body part, selected by the user, of a second particular person, selected by the user, with corresponding local body fate information measured from the second body part of the user.

To achieve at least the above and/or other aspects and advantages, embodiments of the present invention include a body fat measurement result providing method, the method including, maintaining a body fat information database having stored therein at least one particular person's body fat information, which includes local body fat information for at least one body part of the at least one particular person, measuring a user's local body fat for at least one body part of the user, providing the user with a particular person list including the at least one particular person via a predetermined user interface, prompting the user to select a first particular person from the particular person list, generating a first measurement result information, by comparing the user's local body fat measured for the at least one body part of the user, with corresponding local body fat information for the at least one body part of the first particular person, when the selection for the first particular person is received from the user, prompting the user to select a body part and a second particular person from the particular person list when the selection of the first particular person is not received from the user, and generating a second measurement result information by comparing the user's local body fat for the selected body part with the second particular person's local body fat for the selected body part, and outputting the first measurement result information or the second measurement result information.

To achieve at least the above and/or other aspects and advantages, embodiments of the present invention include at least one medium including computer readable code to control at least one processing element in a computer to implement a method of providing a body fat measurement result, the method including, maintaining a body fat information database having stored therein at least one particular person's body fat information which includes local body fat information for at least one body part of the at least one particular person, measuring a user's local body fat for at least one body part of the user, providing the user with a particular person list including the at least one particular person via a predetermined user interface, prompting the user to select a first particular person from the particular person list, generating a first measurement result information by comparing the user's local body fat measured for the at least one body part of the user, with corresponding local body fat information for the at least one body part of the first particular person, when the selection for the first particular person is received from the user, prompting the user to select a body part and a second particular person from the particular person list when the selection of the first particular person is not received from the user, and generating a second measurement result information by comparing the user's local body fat for the selected body part with the second particular person's local body fat for the selected body part, and outputting the first measurement result information or the second measurement result information.

To achieve at least the above and/or other aspects and advantages, embodiments of the present invention include a body fat measurement device, the device including, a body fat information database having stored therein at least one particular person's body fat information which includes local body fat information for at least one body part of the at least one particular person, a user interface providing a user with a particular person list including the at least one particular person and prompting the user to select a first particular person from the particular person list, an information controller generating a first measurement result information, by comparing the user's local body fat measured for the at least one body part of the user, with corresponding local body fat information for the at least one body part of the first particular person when the selection for the first particular person is received from the user, prompting the user to select a body part and a second particular person from the particular person list when the selection of the first particular person is not received from the user, and generating a second measurement result information by comparing the user's local body fat for the selected body part with the second particular person's local body fat for the selected body part, and an output unit outputting the first measurement result information or the second measurement result information.

To achieve at least the above and/or other aspects and advantages, embodiments of the present invention include a portable body fat measurement device, the device including an information controller to generate measurement result information obtained by comparing local body fat information measured from a body part of a user with corresponding body fat information for a particular person selected by the user, and an output unit to output the measurement result to the user.

To achieve at least the above and/or other aspects and advantages, embodiments of the present invention include a body fat measurement result providing method, the method including generating a measurement result information by comparing local body fat information measured from a body part of a user with corresponding body fat information for a particular person selected by the user, and outputting the measurement result information.

BRIEF DESCRIPTION OF THE DRAWINGS

These and/or other aspects and advantages will become apparent and more readily appreciated from the following description of the embodiments, taken in conjunction with the accompanying drawings of which:

FIG. 2 illustrates an example of particular person's body fat information, according to the present invention;

FIG. 5 illustrates an example of first measurement result information, generated according to the first embodiment of the present invention;

DETAILED DESCRIPTION OF EMBODIMENTS

Figure 1:
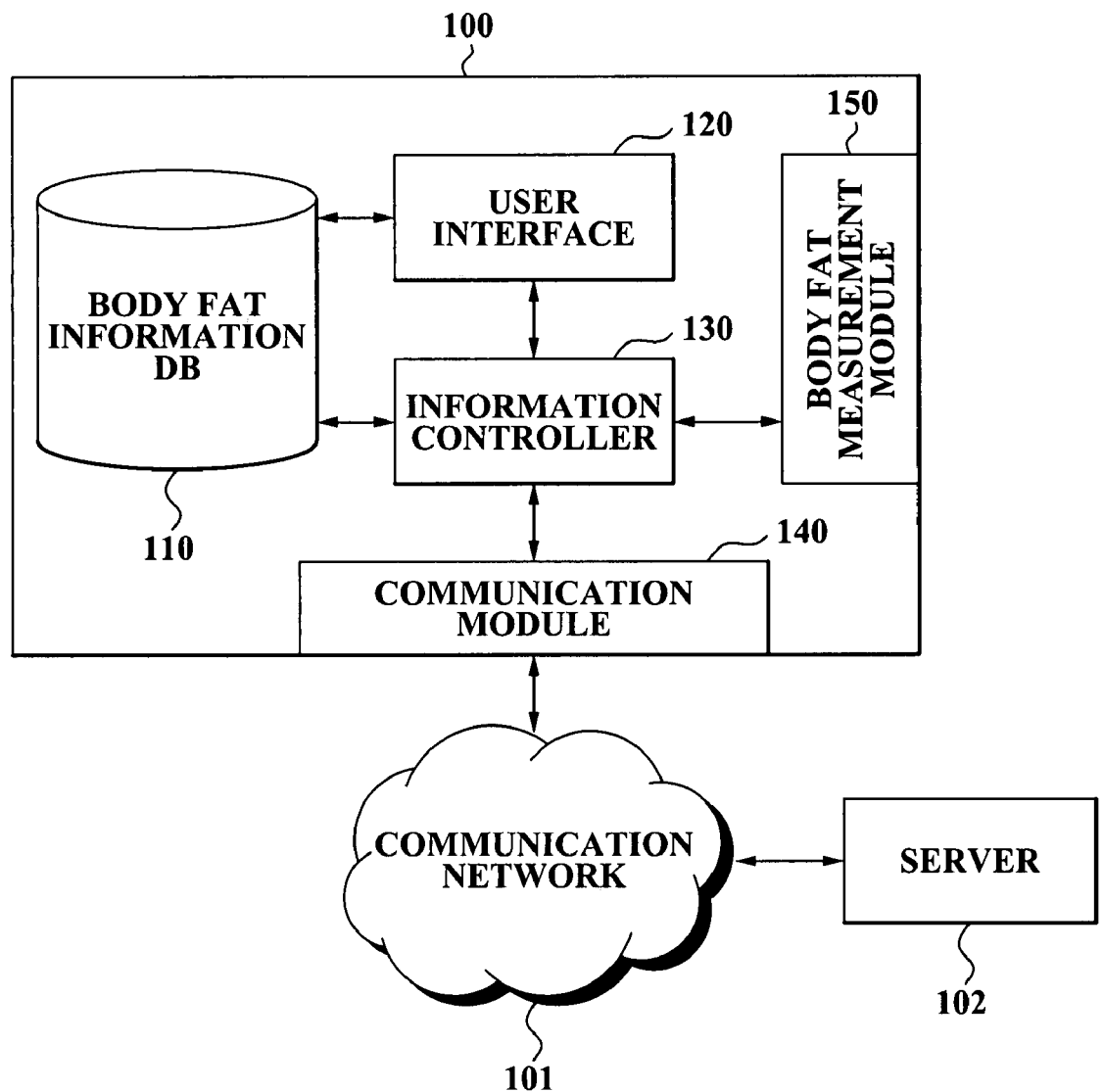
FIG. 1 illustrates a body fat measurement device, according to the present invention.

Reference will now be made in detail to embodiments, examples of which are illustrated in the accompanying drawings, wherein like reference numerals refer to the like elements throughout. Embodiments are described below to explain the present invention by referring to the figures.

FIG. 1 illustrates a body fat measurement device 100, according to the present invention.

The body fat measurement device 100 may include, for example, a body fat information database 110, a user interface 120, an information controller 130, a communication module 140, and a body fat measurement module 150.

The body fat information database 110 may maintain particular person's body fat information with respect to at least one particular person, the particular person's body fat information including local body fat information, corresponding to each of at least one body part of each of the at least one particular person. Namely, at least one particular person's body fat information may be recorded in the body fat information database 110, and the at least one particular person's body fat information may include local body fat information, i.e., body fat information for one or more body parts, as will be described in greater detail with reference to FIG. 2.

FIG. 2 illustrates an example of particular person's body fat information, according to the present invention.

As an example of one particular person's body fat information among a plurality of particular person's body fat information, Beyonce's body fat information is illustrated in FIG. 2. As illustrated in FIG. 2, in the plurality of particular person's body fat information, local body fat information may be recorded corresponding to at least one body part, for a variety of body parts. Specifically, with respect to the particular person's body fat information, local body fat information measuring 6.3 mm may be recorded corresponding to the particular person's neck body fat measurement, and local body fat information measuring 9.8 mm may be recorded in correspondence to the triceps of the particular person. As illustrated in FIG. 2, the local body fat information may be embodied as text, as a figure, or as a predetermined graph, graphic symbol, or voice prompt.

Referring back to FIG. 1, the particular person's body fat information, recorded in the body fat information database 110, may be received, e.g., from an external server 102. Namely, those skilled in the art may embody the body fat measurement device and the body fat measurement result providing method that may be performed on the external server 102, including the plurality of particular person's body fat information, the body fat measurement device 100 may receive the at least one particular person's body fat information from the external server 102 via the communication module 140, and may record the received at least one particular person's body fat information in the body fat information database 110. The particular person's body fat information may be promptly updated in the body fat information database 110 by immediately downloading the particular person's body fat information.

In order to receive the particular person's body fat information from the external server 102, the communication module 140 may include various types of short range communication modules, e.g., a Bluetooth module, a Zigbee module, and the like. Also, in an embodiment in which the body fat measurement device 100 is installed within a predetermined mobile terminal, the communication module 140 may be embodied as a mobile communication module of the predetermined mobile terminal. Accordingly, a communication network 101 may be embodied as various mobile communication networks, such as a Bluetooth network and a Zigbee network utilized by the short range communication module, and, e.g., a code division multiple access (CDMA) network.

The user interface 120 may provide a user with a particular person list having data for at least one particular person, and may receive a selection from the user for a first particular person found among the particular person list, or receive a selection from the user corresponding to at least one body part of at least one particular person.

The present invention may be divided into a first embodiment and a second embodiment. A first embodiment corresponds to when a user selects a first particular person from among the particular person list, and the second embodiment corresponds to when a user selects a particular person corresponding to at least one particular body part from among the particular person list.

Figure 3:
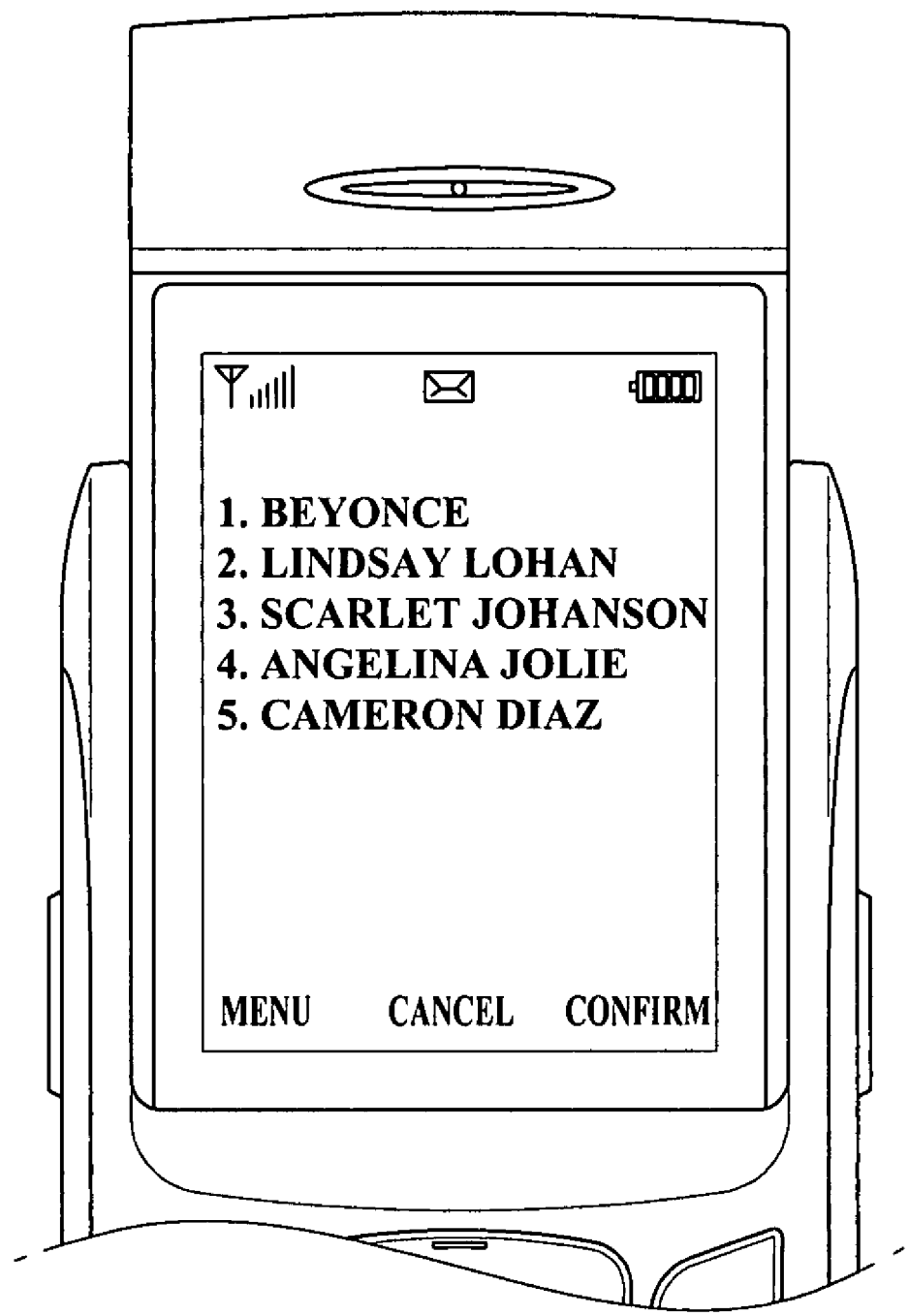
FIG. 3 illustrates a list for a particular person displayed on a user interface, according to a first embodiment of the present invention.

FIG. 3 illustrates a particular person list displayed on a user interface according to a first embodiment of the present invention.

According to the first embodiment of the present invention, the user may select a first particular person among the particular person list displayed on the user interface 120 of FIG. 1. Namely, the user may select a first particular person who has a body shape that the user wants to emulate or resemble, among a plurality of particular people included in the particular person list. Specifically, as illustrated in FIG. 3 and as an example, the user may select a single particular person among five particular people including, 'Beyonce', 'Lindsay Lohan', 'Scarlet Johanson', 'Angelina Jolie', and 'Cameron Diaz', displayed on the user interface 120 of FIG. 1. In the first embodiment of the present invention, the user's local body fat may be compared with the first particular person's local body fat, and the comparison result may be provided to the user, which will be described later in greater detail.

Figure 4:
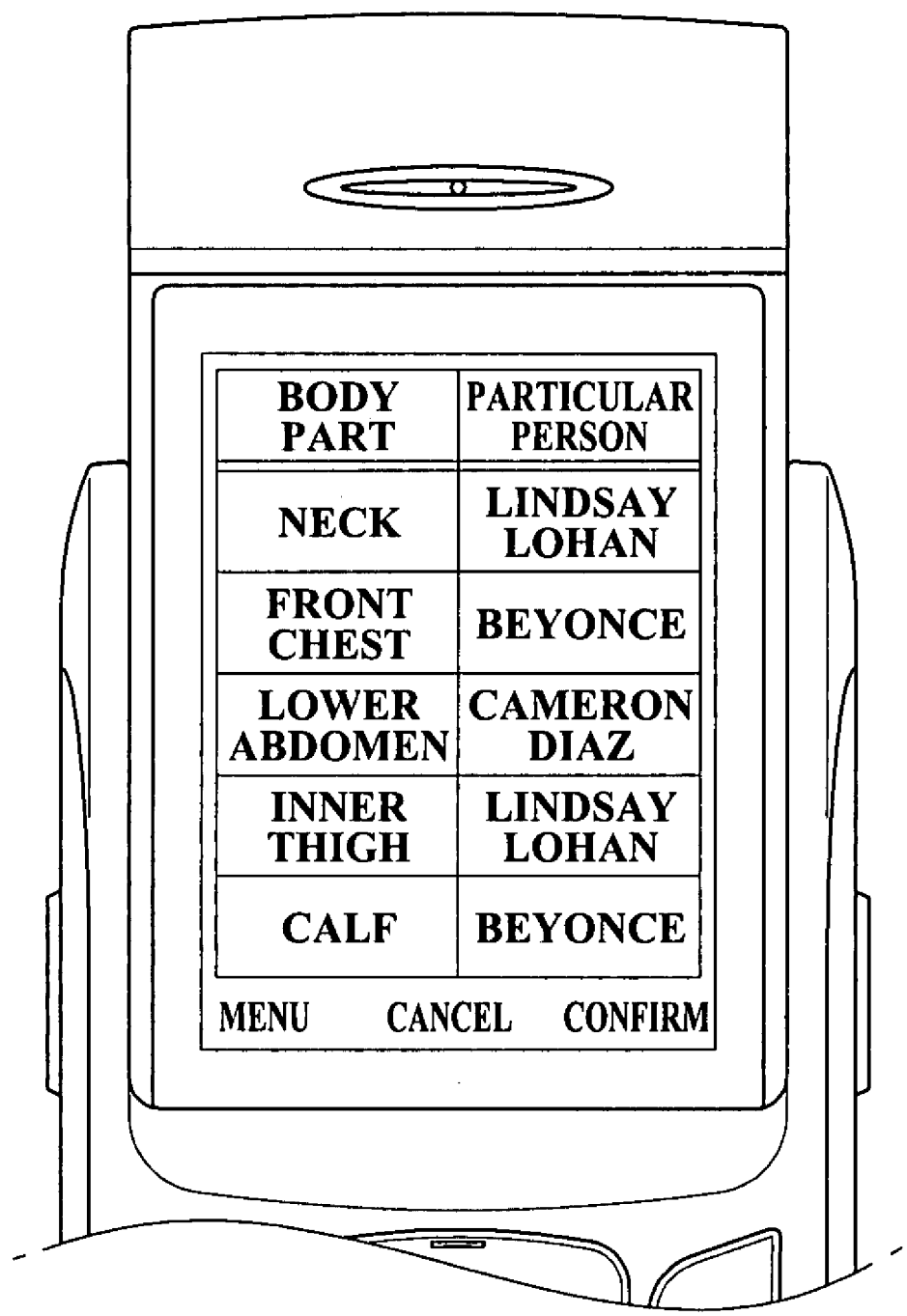
FIG. 4 illustrates a body part and a list for a particular person displayed on a user interface, according to a second embodiment of the present invention.

FIG. 4 illustrates a list including various body parts and a particular person list displayed on a user interface 120, according to a second embodiment of the present invention.

According to the second embodiment of the present invention, at least one body part list and a particular person list may be displayed on the user interface 120. A user may select a body part that the user wants to measure from the at least one body part list. As an example, the user may select any body part, such as a neck, a front chest, a lower abdomen, an inner thigh, or a calf.

The user interface 120 may receive a selection of a particular person from the user, corresponding to each of the selected body parts. Namely, the user interface 120 may provide the user with the particular person list, including a plurality of particular people, corresponding to e.g., a neck. The user may then select, e.g., 'Lindsay Lohan' as the particular person corresponding to the neck. Also, the user interface 120 may provide the user with a particular person list including a plurality of particular people, corresponding to, e.g., a front chest, and receive from the user, e.g., Beyonce' as the particular person corresponding to the front chest.

According to the second embodiment of the present invention, the user may select one or more particular people among the particular person list, for each of the body parts, instead of selecting a single particular person as described in the first embodiment of the present invention. In the second embodiment of the present invention, a measurement result may be provided to the user, the measurement result comparing the user's local body fat with a particular person's local body fat information, the particular person having been selected by the user for at least one particular body part.

Referring back to FIG. 1, the body fat measurement module 150 may be used to measure local body fat of the at least one body part of the user. The body fat measurement module 150 may include, e.g., an optical sensor module in order to measure the local body fat. The local body fat of the at least one body part of the user may be measured using the optical sensor module. The optical sensor module may measure local body fat by irradiating at least one body part with light, where the irradiated light is scattered inside of the at least one body part, the scattered light returns, and the returning light is received by the optical sensor module. Accordingly, the body fat measurement module 150 may measure the local body fat using the optical sensor, but may also equally measure the user's local body fat with respect to each of at least one body part using all various body fat measurement devices used in the art.

The information controller 130 may generate measurement result information using the user's local body fat information and the particular person's local body fat information. The information controller 130 may generate first measurement result information, according to the first embodiment of the present invention, and may generate second measurement result information, according to the second embodiment of the present invention.

According to the first embodiment of the present invention, the information controller 130 may generate the first measurement result information, when a selection for a first particular person is received from the user, by comparing the user's local body fat, having been measured with respect to each of at least one body part of the user, with the first particular person's local body fat, corresponding to each of at least one body part of the first particular person's body fat information.

Namely, the information controller 130 may read the first particular person's body fat information from the body fat information database 110 when the user selects the first particular person among the particular person list via the user interface 120.

The information controller 130 may generate the first measurement result information by comparing, for each body part, the user's local body fat, having been measured with respect to each of at least one body part of the user with the local body fat information for each body part, included in the first particular person's body fat information, which will be described in more detail by referring to FIG. 5.

FIG. 5 illustrates an example of first measurement result information, generated according to the first embodiment of the present invention.

According to the first embodiment of the present invention, as illustrated in FIG. 5, the information controller 130 of FIG. 1 may generate the first measurement result information by comparing, for each body part, the user's local body fat with the first particular person's local body fat. Namely, the information controller 130 may generate the first measurement result information by comparing the user's local body fat with the local body fat information, included in the first particular person's body fat information, having been read from the body fat information database 110 of FIG. 1, for each body part.

As an example, the information controller 130 may generate the first measurement result information by comparing the user's local body fat value with a first particular person's local body fat value via a graph. Here, continuing the example, Beyonce's neck, having a local body fat value of 6.3 mm, is compared to the user's local body fat value via a graph.

In addition to the neck, the information controller 130 may generate the first measurement result information by comparing the user's local body fat values with the first particular person's local body fat values for all body parts via a graph.

The information controller 130 may generate the first measurement result information comparing local body fat data for each body part via, e.g., a graph or via a predetermined graphic. As an example, when the selected first particular person is Beyonce, the information controller 130 may generate the first measurement result information by synthesizing the user's photo with Beyonce's virtual figure graphically. The synthesis may be performed for the entire body or for individually selected body parts.

Namely, the information controller 130 may provide the user with a synthesized figure graphic by synthesizing the actual photo of the user with a graphic image of Beyonce, using a difference between the local body fat of the user and Beyonce, for each body part. Here, the user may effectively manage his or her body fat using the comparison results, which provide constant feedback and motivate the user to exercise harder by providing the first measurement result information, including the synthesized graphic.

Also, the information controller 130 may generate first measurement result information using a predetermined text or a voice in addition to the first measurement result information provided via graph and/or graphically. Namely, the information controller 130 may generate the first measurement result information by comparing, for each of at least one body part, the user's local body fat with the first particular person's local body fat, via a predetermined text, and may generate the first measurement result information explaining the comparison result using a predetermined voice. The comparison result, included in the first measurement result information, may be communicated to the user via any one or more of graph, graphic, text, voice, and the like, according to a determination by those skilled in the art.

Referring back to FIG. 1, the information controller 130 may generate second measurement result information by comparing the user's local body fat, having been measured with respect to each of at least one user body part, with the particular person's local body fat, having been received for each of at least one body part, according to the second embodiment of the present invention.

The information controller 130 may read the particular person's body fat information from the body fat information database 110 when a selection for the particular person, for each of at least one body part, is received from the user via the user interface 120. The information controller 130 may generate the second measurement result information by comparing the measured user's local body fat in each body part with the local body fat information of a plurality of particular persons, which will be described in detail by referring to FIG. 6.

Figure 6:
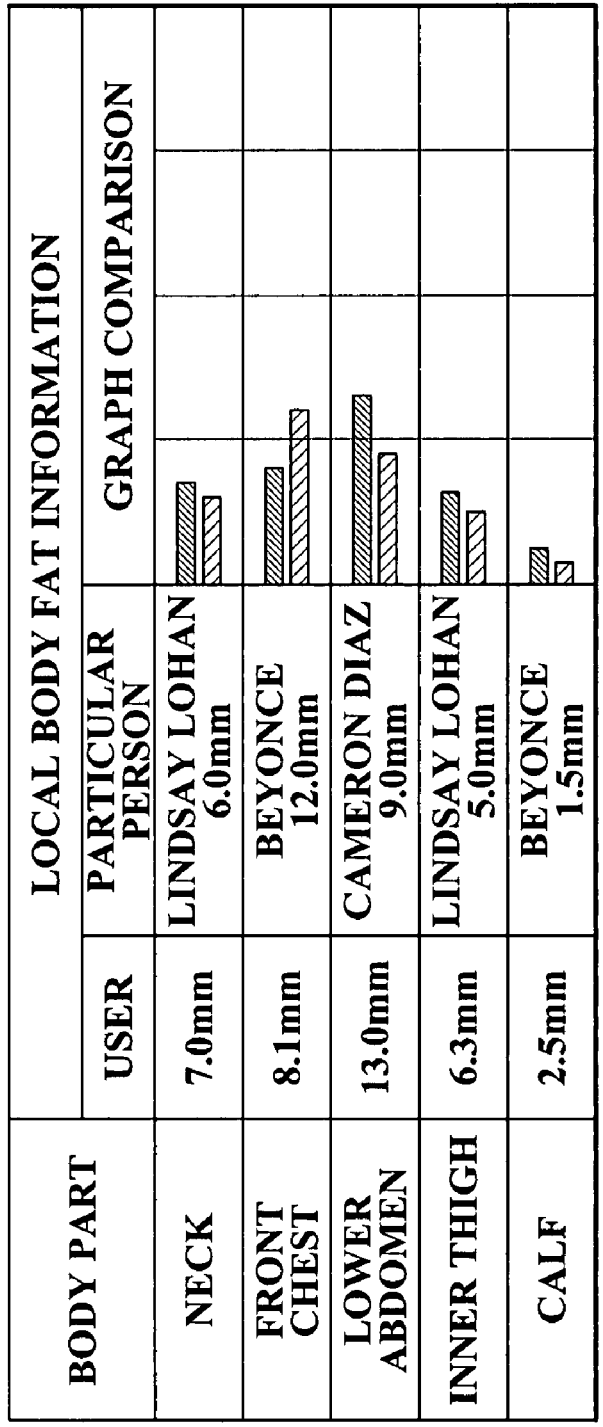
FIG. 6 illustrates an example of second measurement result information, generated according to the second embodiment of the present invention.

FIG. 6 illustrates an example of second measurement result information, generated according to the second embodiment of the present invention.

According to the second embodiment of the present invention, the information controller 130 may generate second measurement result information. Namely, the information controller 130 may read local body fat information, corresponding to each body part, from the particular person's body fat information in order to generate the second measurement result information, the particular person's body fat information being selected by the user for each body part. Later, the information controller 130 may generate the second measurement result information by comparing the measured user's local body fat information with the read particular person's local body fat for each body part.

As an example, when the user selects Angelina Jolie as the particular person corresponding to a neck, the information controller 130 may generate the second measurement result information by comparing a local body fat value measured at the neck of the user with a local body fat value of Angelina Jolie's neck, via a graph.

In addition to the neck, the information controller 130 may generate the second measurement result information via a graph for a plurality of body parts by comparing the user's local body fat values for each and every body part, with a plurality of user-selected particular persons' local body fat values.

The information controller 130 may generate the second measurement result information via the graph, and may generate the measurement result information via a predetermined graphic. As an example, when Beyonce is selected by the user as the particular person corresponding to a front chest, the information controller 130 may generate the second measurement result information by synthesizing a user's front chest photo with a virtual graphic of Beyonce's chest.

In addition, the information controller 130 may generate the second measurement result information by synthesizing all of the particular person's body part figures with each of the user's body part photos. Here, the user may more vigorously manage her body fat since she is motivated to diet and exercise harder by seeing the second measurement result information including the synthesized graphic.

Also, the information controller 130 may generate the second measurement result information using a predetermined text or a predetermined voice, in addition to the second measurement result information provided via graph and/or graphically. Namely, the information controller 103 may generate the second measurement result information by comparing, for each of at least one body part, the user's local body fat with the particular person's local body fat, using predetermined text, and may generate the second measurement result information, explaining the comparison result using a predetermined voice. The comparison result, included in the second measurement result information, may be communicated to the user via any one or more of graph, graphic, text, voice, and the like, according to a determination by those skilled in the art.

Referring back to FIG. 1, the body fat measurement device 100 may operate to embody a third embodiment of the present invention, in addition to the first and second embodiments. The third embodiment may be embodied to include both the first embodiment and the second embodiment.

Namely, the body fat information database 110 may maintain, with respect to at least one particular person, the particular person's body fat information, including local body fat information corresponding to each of at least one body part of each of the at least one particular person. The particular person's body fat information may be immediately updated by receiving the particular person's body fat information from the external server 102 via the communication network 101 and the communication module 140.

The user interface 120 may provide a user with a particular person list to allow selection of the at least one particular person, and may receive a user selection of a first particular person, from among the particular person list, or receive a selection from the user of a particular person corresponding to each of the at least one body part. Namely, the user interface 120 may receive the selection for the first particular person as described in the first embodiment, and may receive the selection for the particular person corresponding to each of the at least one body part described in the second embodiment.

The body fat measurement module 150 may measure local body fat of at least one body part of the user.

The information controller 130 may generate first measurement result information by comparing the user's local body fat, having been measured with respect to the each of the at least one body part of the user, with a first particular person's local body fat, corresponding to each of the at least one body part of the first particular person, when the selection for the first particular person is received from the user via the user interface 120.

Also, the information controller 130 may generate a second measurement result information by comparing the user's local body fat, having been measured with respect to each of the at least one body part of the user, with the particular person's local body fat, having been received corresponding to each of the at least one body part of the particular person, when the selection for the particular person, corresponding to each of the at least one body part, is received from the user via the user interface 120.

The information controller 130 may control the user interface 120 to display or play the first measurement result information or the second measurement result information via the user interface 120. The first measurement result information or the second measurement result information may be embodied by including any one or more of predetermined graph measurement result information, predetermined graphic measurement result information, predetermined text measurement result information, and predetermined voice measurement result information, as described in the first embodiment and the second embodiment.

As described above, the structure and operation of a body fat measurement device 100, according to one or more embodiments of the present invention are described by referring to FIGS. 1 through 6.

Hereinafter, a body fat measurement result providing method of the present invention which may be embodied by the body fat measurement device 100 will be described by referring to FIGS. 7 through 9. Alternatively, the body fat measurement result providing method may equally be performed by other body fat measurement devices not previously described herein. The body fat measurement result providing method may be divided, for example, into a first embodiment, a second embodiment, and a third embodiment.

Figure 7:
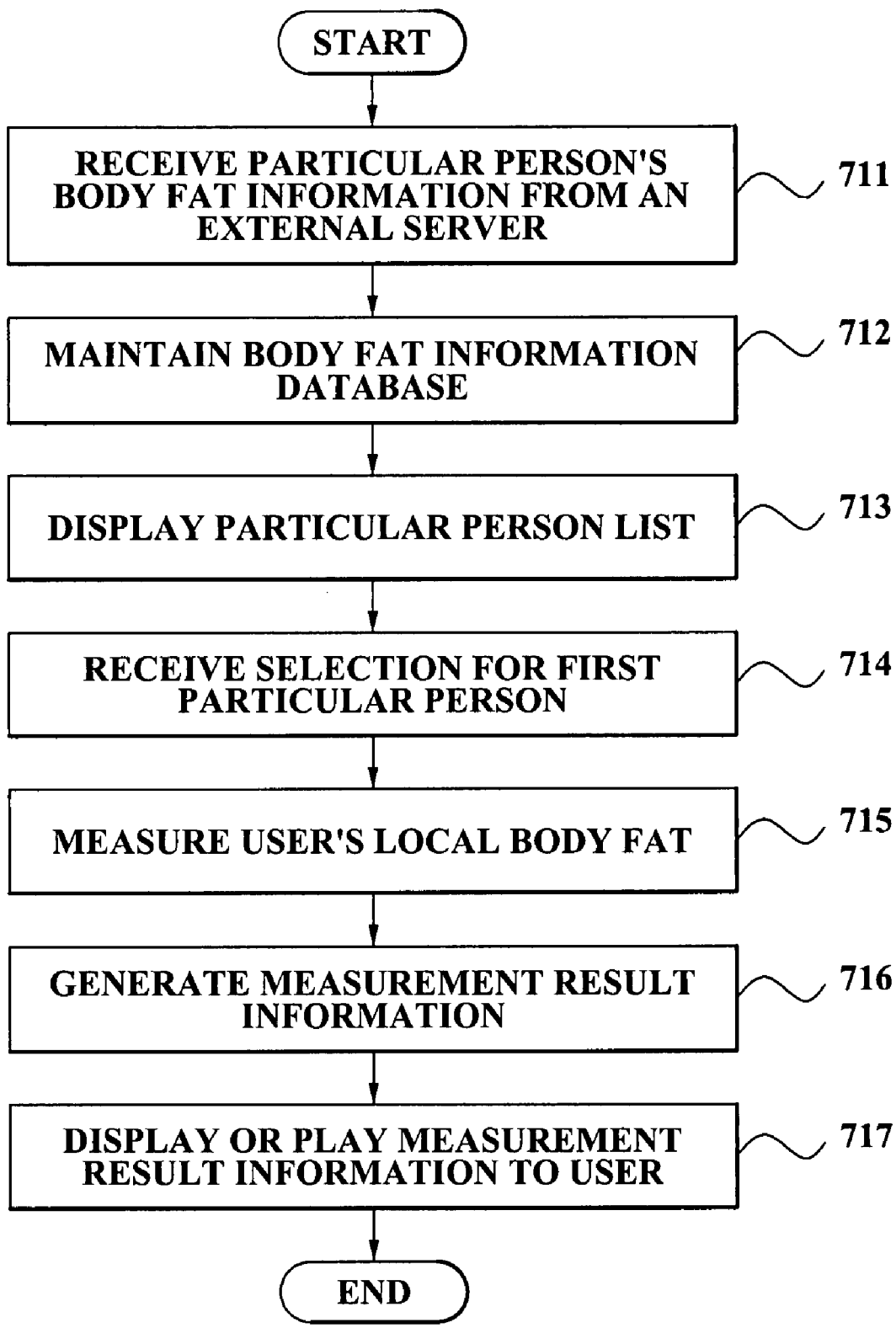
FIG. 7 illustrates a method of providing body fat measurement result, according to the first embodiment of the present invention.

FIG. 7 illustrates a method of providing body fat measurement results according to the first embodiment of the present invention.

In operation 711, a body fat measurement device, according to an embodiment of the present invention may receive a particular person's body fat information from an external server. In operation 712, the body fat measurement device may record the received particular person's body fat information, and maintain a body fat information database that includes local body fat information corresponding to each of at least one body part of the at least one particular person.

In operation 713, the body fat measurement device may provide a user, via a user interface, with a particular person list for the at least one particular person data stored in the body fat information database. In operation 714, the body fat measurement device may receive from the user, via the user interface, a selection for a first particular person, selected from among the particular person list.

In operation 715, the body fat measurement device may measure local body fat with respect to each of at least one body part of the user. In operation 716, the body fat measurement device may generate measurement result information by comparing a user's local body fat, having been measured with respect to each of at least one body part of the user, with a first particular person's local body fat, corresponding to each of at least one body part of the first particular person's body fat information.

In operation 717, the body fat measurement device may display or play the generated measurement result information to the user via the user interface.

Figure 8:
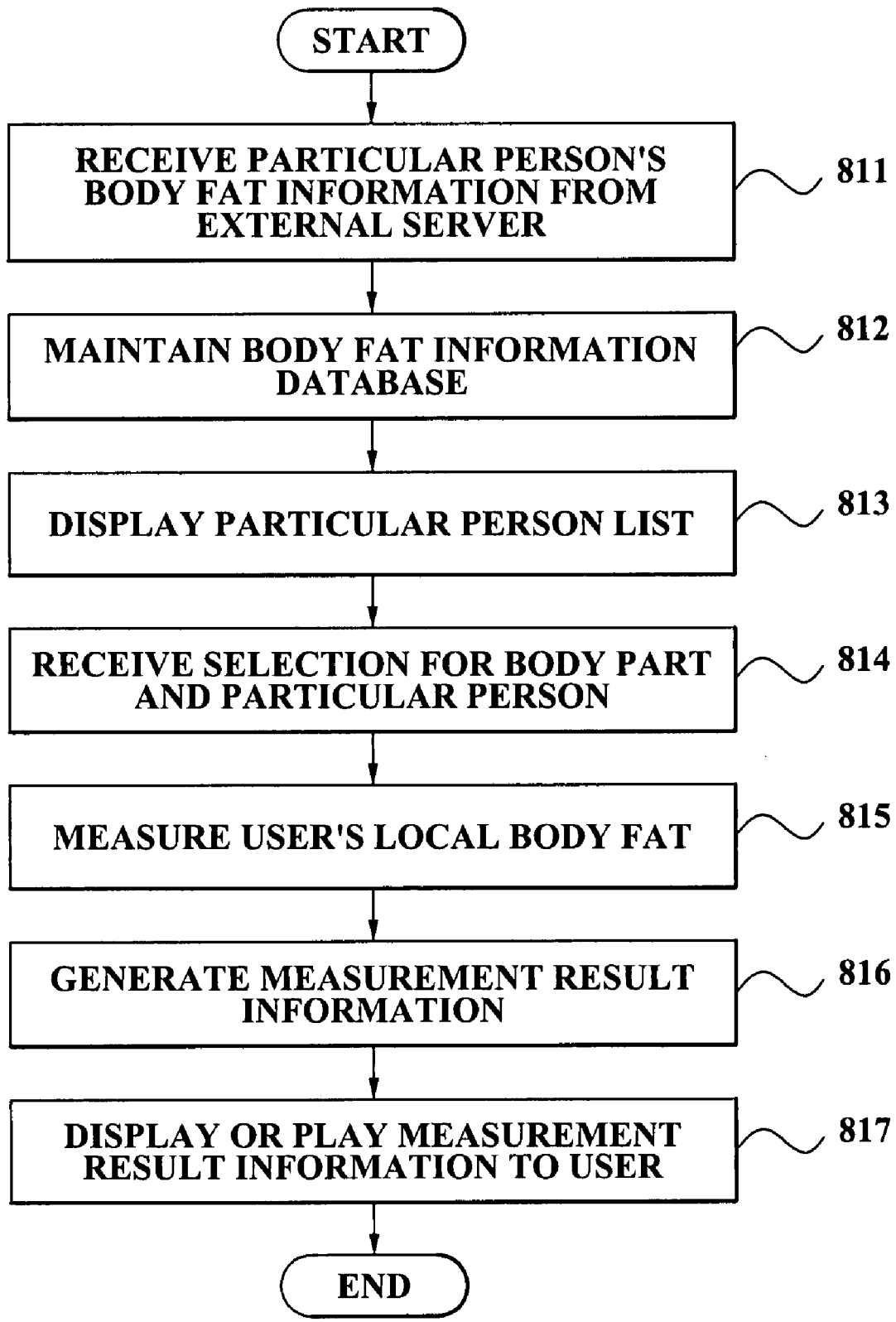
FIG. 8 illustrates a method of providing body fat measurement result, according to the second embodiment of the present invention.

FIG. 8 illustrates a body fat measurement result providing method according to the second embodiment of the present invention.

In operation 811, the body fat measurement device, according to the second embodiment of the present invention may receive a particular person's body fat information for at least one particular person from an external server. In operation 812, the body fat measurement device may record the received particular person's body fat information, and maintain a body fat information database for the at least one particular person. The body fat information database may store data having the at least one particular person's body fat information which may include local body fat information corresponding to each of at least one body part of the at least one particular person.

In operation 813, the body fat measurement device may provide a user, via a user interface, with a particular person list including the at least one particular person stored in the body fat information database. In operation 814, the body fat measurement device 100 may receive from the user, via the user interface, a selection for a particular person, among the particular person list.

In operation 815, the body fat measurement device may measure local body fat, corresponding to each of the at least one body part received from the user. In operation 816, the body fat measurement device may generate measurement result information by comparing a user's local body fat, having been measured with respect to each of at least one body part of the user, with a particular person's local body fat, corresponding to each of at least one body part of the particular person's body fat information.

In operation 817, the body fat measurement device may display or play the generated measurement result information to the user via the user interface.

Figure 9:
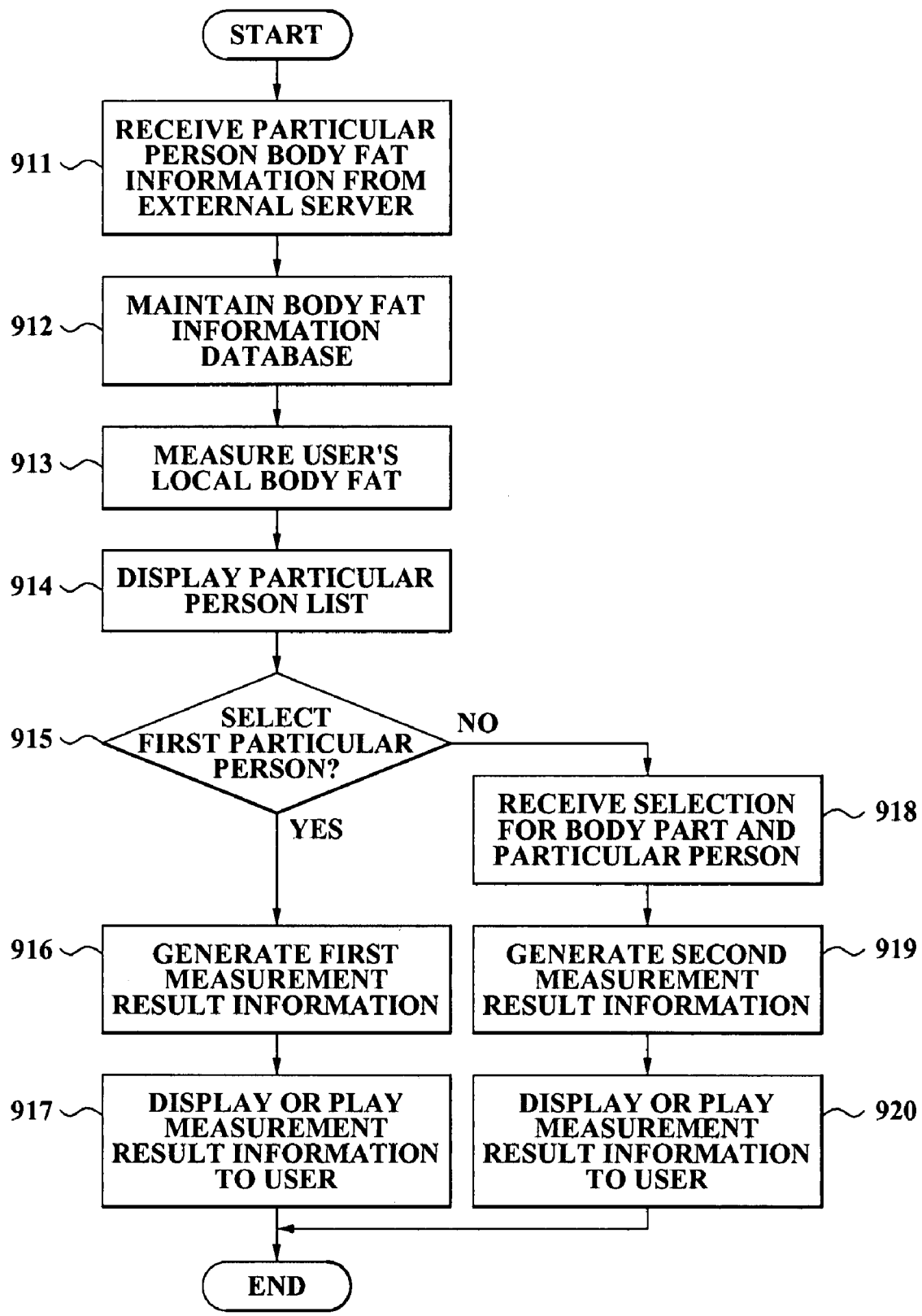
FIG. 9 illustrates a body fat measurement result providing method, according to a third embodiment of the present invention.

FIG. 9 illustrates a body fat measurement result providing method according to a third embodiment of the present invention.

In operation 911, the body fat measurement device may receive a particular person's body fat information for at least one particular person from an external server. In operation 912, the body fat measurement device may record the received particular person's body fat information, and maintain a body fat information database for the at least one particular person. The body fat information database may store data having the at least one particular person's body fat information which may include local body fat information corresponding to each of at least one body part of the at least one particular person.

In operation 913, the body fat measurement device 100 may measure local body fat for each of at least one body part of the user. In operation 914, the body fat measurement device may provide the user, via a user interface, with a particular person list for the at least one particular person data stored in the body fat information database.

When a selection for a first particular person is received from the user among the particular person list, in operation 915, the body fat measurement device may generate first measurement result information by comparing the users local body fat, having been measured with respect to each of the at least one body part of the user, with the first particular person's local body fat, corresponding to each of the at least one body part of the first particular person in operation 916. In operation 917, the body fat measurement device may display or play the generated first measurement result information to the user via the user interface.

In operation 918, the body fat measurement device may receive a selection for a particular person from the user corresponding to each of at least one body part via the user interface when the first particular person is not selected by the user, among the particular person list, in operation 915. The body fat measurement device may generate second measurement result information by comparing the user's local body fat, having been measured with respect to each of the at least one body part of the user, with a particular person's local body fat, having been received corresponding to each of the at least one body part of the particular person, in operation 919. The body fat measurement device may display or play the generated second measurement result information to the user via the user interface in operation 920.

As described in FIGS. 7 through 9, it is obvious to those skilled in the art that the body fat measurement result providing method according to the first embodiment through third embodiment of the present invention may be embodied by including some or all embodiments of the body fat measurement device 100 according to the first embodiment through third embodiment of the present invention.

In addition to the above described embodiments, embodiments of the present invention may also be implemented through computer readable code/instructions in/on a medium, e.g., a computer readable medium, to control at least one processing element to implement any above described embodiment. The medium can correspond to any medium/media permitting the storing of the computer readable code.

The computer readable code may be recorded/transferred on a medium in a variety of ways, with examples of the medium including recording media, such as magnetic storage media (e.g., ROM, floppy disks, hard disks, etc.) and optical recording media (e.g., CD-ROMs, or DVDs). The media may also be a distributed network, so that the computer readable code is stored/transferred and executed in a distributed fashion. Still further, as only an example, the processing element could include a processor or a computer processor, and processing elements may be distributed and/or included in a single device.

A body fat measurement device as has been described herein may be embodied as any one of mobile devices, such as a mobile terminal, a personal digital assistant (PDA), a portable game device, an MP3 player, a personal multimedia player (PMP), and a Digital Multimedia broadcasting (DMB) terminal. Alternatively, the body fat measurement device need not be installed within the above-described mobile devices, but may be designed as a stand-alone device.

According to one or more embodiments of the present invention, a body fat measurement device and a body fat measurement result providing method may encourage a user to effectively control their diet and to steadily exercise to manage body fat, since local body fat of the user may be compared for each body part with a local body fat of a particular person selected by the user, and the comparison result may be provided to the user.

Also, according to one or more embodiments of the present invention, a body fat measurement device and a body fat measurement result providing method may encourage a user to effectively control their diet and to steadily exercise to manage body fat since local body fat of a user may be compared for each body part with local body fat of a particular person, selected by the user, the comparison result may be provided to the user, and a user's desire to respectively look like a particular person for the each body part may thus be satisfied.

Also, according to one or more embodiments of the present invention, a body fat measurement device and a body fat measurement result providing method may encourage a user to effectively control their diet and to steadily exercise to manage a body shape since local body fat of a user may be compared for each body part with a local body fat of a particular person selected by the user, and the comparison result may be provided to the user via a predetermined graph, a predetermined graphic, a predetermined text, or a predetermined voice.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A body fat measurement result providing method, the method comprising:
   maintaining a body fat information database having stored therein at least one particular person's body fat information, which includes local body fat information for at least one body part of the at least one particular person who is identified by name;
   providing a user with a particular person list including the name of the at least one particular person, and receiving a selection from the user of a first particular person who is identified by name and is selected from the particular person list, the first particular person being someone other than the user; and
   generating a measurement result information, using a body fat measurement device, by comparing the user's local body fat measured with the body fat measurement device for at least one body part of the user, with corresponding local body fat information, obtained from the body fat information database, for the at least one body part of the first particular person who is identified by name.

2. The method of claim 1, wherein the maintaining of the body fat information database comprises:
   receiving the at least one particular person's body fat information from a predetermined server.

3. The method of claim 1, wherein the generating of the measurement result information comprises:
   generating graph measurement result information by comparing, for the at least one body part, a user's local body fat with the first particular person's local body fat via a predetermined graph.

4. The method of claim 1, wherein the generating of the measurement result information comprises:
   generating graphic measurement result information by comparing, for the at least one body part, the user's local body fat with the first particular person's local body fat via a predetermined graphic.

5. The method of claim 1, wherein the generating of the measurement result information comprises:
   generating text measurement result information by comparing, for the at least one body part, the user's local body fat with the first particular person's local body fat via a predetermined text.

6. The method of claim 1, wherein the generating of the measurement result information comprises:
   generating voice measurement result information by comparing, for the at least one body part, the user's local body fat with the first particular person's local body fat via a predetermined voice.

7. The method of claim 1, further comprising:
   controlling the measurement result information to be displayed or played via a user interface.

8. A body fat measurement result providing method, the method comprising:
   maintaining a body fat information database having stored therein at least one particular person's body fat information which includes local body fat information for at least one body part of the at least one particular person who is identified by name;
   providing a user with a particular person list, including the name of the at least one particular person, via a predetermined user interface, and receiving a selection from the user for at least one body part and at least one particular person from the particular person list;
   generating a measurement result information, with a body fat measurement device, by comparing local body fat information of a first body part, selected by the user, of a first particular person, selected by the user and who is not the user, with corresponding local body fat information measured from the first body part of the user using the body fat measurement device, and by comparing local body fat information of a second body part, selected by the user, of a second particular person, selected by the user and who is different than the first particular person, with corresponding local body fat information measured from the second body part of the user.

9. The method of claim 8, wherein the maintaining of the body fat information database comprises:
   receiving the at least one particular person's body fat information with respect to the at least one particular person from a predetermined server.

10. The method of claim 8, wherein the generating of the measurement result information comprises:
    generating graph measurement result information by comparing the first body part of the first particular person with corresponding local body fat information measured from the first body part of the user via a predetermined graph.

11. The method of claim 8, wherein the generating of the measurement result information comprises:
    generating graphic measurement result information by comparing the first body part of the first particular person with corresponding local body fat information measured from the first body part of the user via a predetermined graphic.

12. The method of claim 8, wherein the generating of the measurement result information comprises:
    generating text measurement result information by comparing the first body part of the first particular person with corresponding local body fat information measured from the first body part of the user via a predetermined text.

13. The method of claim 8, wherein the generating of the measurement result information comprises:
generating voice measurement result information by comparing the first body part of the first particular person with corresponding local body fat information measured from the first body part of the user via a predetermined voice.

14. The method of claim 8, further comprising:
controlling the measurement result information to be displayed or played via a user interface.

15. A body fat measurement result providing method, the method comprising:
maintaining a body fat information database having stored therein at least one particular person's body fat information, which includes local body fat information for at least one body part of the at least one particular person who is identified by name;
measuring a user's local body fat for at least one body part of the user;
providing the user with a particular person list including the name of the at least one particular person via a predetermined user interface;
prompting the user to select a first particular person who is identified by name from the particular person list and is someone other than the user;
generating a first measurement result information, by comparing the user's local body fat measured with a body fat measurement device for the at least one body part of the user, with corresponding local body fat information for the at least one body part of the first particular person, when the selection for the first particular person is received from the user;
prompting the user to select a body part and a second particular person from the particular person list when the selection of the first particular person is not received from the user, and generating a second measurement result information by comparing the user's local body fat for the selected body part with the second particular person's local body fat for the selected body part; and
outputting, via the body fat measurement device, the first measurement result information or the second measurement result information.

16. The method of claim 15, wherein the maintaining of the body fat information database comprises:
receiving the at least one particular person's body fat information from a predetermined server.

17. The method of claim 15, wherein the first measurement result information or the second measurement result information comprises predetermined graph measurement result information, predetermined graphic measurement result information, predetermined text measurement result information, or predetermined voice measurement result information.

18. The method of claim 15, further comprising:
controlling the first measurement result information or the second measurement result information to be displayed or played via a user interface.

19. At least one non-transitory computer readable medium comprising computer readable code to control at least one processing element in a computer to implement a method of providing a body fat measurement result, the method comprising:
maintaining a body fat information database having stored therein at least one particular person's body fat information which includes local body fat information for at least one body part of the at least one particular person who is identified by name and is someone other than the user;
measuring a user's local body fat for at least one body part of the user;
providing the user with a particular person list including the name of the at least one particular person via a predetermined user interface;
prompting the user to select a first particular person from the particular person list;
generating a first measurement result information by comparing the user's local body fat measured with a body fat measurement device for the at least one body part of the user, with corresponding local body fat information for the at least one body part of the first particular person, when the selection for the first particular person is received from the user;
prompting the user to select a body part and a second particular person from the particular person list when the selection of the first particular person is not received from the user, and generating a second measurement result information by comparing the user's local body fat for the selected body part with the second particular person's local body fat for the selected body part; and
outputting, via the body fat measurement device, the first measurement result information or the second measurement result information.

20. A body fat measurement device, the device comprising:
a body fat information database having stored therein at least one particular person's body fat information which includes local body fat information for at least one body part of the at least one particular person who is identified by name and is someone other than the user;
a user interface providing a user with a particular person list including the name of the at least one particular person and -prompting the user to select a first particular person from the particular person list;
an information controller generating a first measurement result information, by comparing the user's local body fat measured for the at least one body part of the user, with corresponding local body fat information for the at least one body part of the first particular person when the selection for the first particular person is received from the user, prompting the user to select a body part and a second particular person from the particular person list when the selection of the first particular person is not received from the user, and generating a second measurement result information by comparing the user's local body fat for the selected body part with the second particular person's local body fat for the selected body part; and
an output unit outputting the first measurement result information or the second measurement result information.

21. The device of claim 20, further comprising:
a communication module receiving the at least one particular person's body fat information from a predetermined server; and
a body fat measurement module measuring a user's local body fat for at least one body part of the user.

22. The device of claim 20, wherein the first measurement result information or the second measurement result information comprises:
predetermined graph measurement result information, predetermined graphic measurement result information, predetermined text measurement result information, and predetermined voice measurement result information, and the first measurement result information or the second measurement result information controls the first measurement result information or the second measurement result information to be displayed or played via a user interface.

23. A portable body fat measurement device, the device comprising:

an information controller to generate measurement result information obtained by comparing local body fat information measured from a body part of a user with corresponding local body fat information for a particular person who is someone other than the user and is identified by name and is selected by the user; and an output unit to output the measurement result to the user.

24. The device of claim 23, further comprising:

a body fat information database having stored therein the at least one particular person's body fat information which includes the local body fat information for the at least one body part of the at least one particular person.

25. The device of claim 23, wherein the corresponding body fat information is for a body part of the particular person that is identical to the body part of the user that is measured.

26. A body fat measurement result providing method, the method comprising:

generating a measurement result information using a body fat measurement device by comparing local body fat information measured from a body part of a user with corresponding local body fat information for a particular person who is someone other than the user and is identified by name and is selected by the user; and outputting, via the body fat measurement device, the measurement result information.

27. The method of claim 26, further comprising:

maintaining a body fat information database having stored therein the at least one particular person's body fat information which includes the local body fat information for the at least one body part of the at least one particular person.

28. The method of claim 26, wherein the corresponding body fat information is for a body part of the particular person that is identical to the body part of the user that is measured.

* * * * *

UNITED STATES PATENT AND TRADEMARK OFFICE
CERTIFICATE OF CORRECTION

| | | |
|---|---|---|
| PATENT NO. | : 7,987,055 B2 | Page 1 of 1 |
| APPLICATION NO. | : 11/976620 | |
| DATED | : July 26, 2011 | |
| INVENTOR(S) | : Sang Kon Bae et al. | |

It is certified that error appears in the above-identified patent and that said Letters Patent is hereby corrected as shown below:

Column 14, Line 35, In Claim 8, delete "person," and insert --person--, therefor.

Column 16, Line 39, In Claim 20, delete "-prompting" and insert --prompting--, therefor.

Signed and Sealed this
Third Day of January, 2012

David J. Kappos
*Director of the United States Patent and Trademark Office*